(12) United States Patent
Hames

(10) Patent No.: US 9,421,117 B1
(45) Date of Patent: Aug. 23, 2016

(54) ANKLE BRACE THAT HEALS AND SUPPORTS THE PLANTAR FASCIA AND ACHILLES TENDON

(71) Applicant: Michael Thomas Hames, Florence, AL (US)

(72) Inventor: Michael Thomas Hames, Florence, AL (US)

(*) Notice: Subject to any disclaimer, the term of this patent is extended or adjusted under 35 U.S.C. 154(b) by 204 days.

(21) Appl. No.: 13/789,260

(22) Filed: Mar. 7, 2013

Related U.S. Application Data

(60) Provisional application No. 61/619,805, filed on Apr. 3, 2012.

(51) Int. Cl.
*A61F 5/01* (2006.01)
*A43B 13/18* (2006.01)
*A43B 13/20* (2006.01)

(52) U.S. Cl.
CPC .............. *A61F 5/0127* (2013.01); *A61F 5/012* (2013.01); *A61F 5/0111* (2013.01); *A43B 13/189* (2013.01); *A43B 13/206* (2013.01); *A61F 5/01* (2013.01)

(58) Field of Classification Search
CPC ........ A61F 5/01; A61F 5/0111; A61F 5/012; A61F 5/0127; A43B 7/14; A43B 7/1495; A43B 13/189; A43B 13/206
USPC ....... 602/13, 23, 27–29, 65; 128/882; 36/43, 36/145, 153
See application file for complete search history.

(56) References Cited

U.S. PATENT DOCUMENTS 5,944,678 A * 8/1999 Hubbard .................... 602/27
6,755,798 B2 * 6/2004 McCarthy et al. .......... 602/13
2007/0283597 A1 * 12/2007 Logan .......................... 36/91

* cited by examiner

*Primary Examiner* — Keri J Nelson
(74) *Attorney, Agent, or Firm* — C. Brandon Browning; Maynard, Cooper & Gale

(57) ABSTRACT

An ankle brace including a foot portion, an ankle portion with a strap for securing the brace to the user and a single pneumatic air bladder system. The air bladder system includes a distal U-shaped chamber which surrounds the user's plantar fascia connected via two tapered communicating channels to two proximal chambers positioned on either side of the user's Achilles tendon. Pressure applied to the distal U-shaped chamber results in air flow to the proximal chambers. Air flows back to the distal chamber when that pressure is released. Expansion and contraction of the distal and proximal chambers massages the underlying plantar fascia and Achilles tendon.

20 Claims, 5 Drawing Sheets

ANKLE BRACE THAT HEALS AND SUPPORTS THE PLANTAR FASCIA AND ACHILLES TENDON

RELATED APPLICATIONS

This application claims priority to U.S. Provisional Patent Application No. 61/619,805, filed on Apr. 3, 2012 and titled, "Ankle Brace that Heals and Supports the Plantar Fascia and Achilles Tendon," the entire contents of which are incorporated herein in their entirety.

FIELD OF INVENTION

The present invention relates to a therapeutic ankle brace for treatment of plantar fasciitis/fasciosis and Achilles tendonitis/tendonosis, and more specifically to a brace that pneumatically massages soft tissue of the foot for relieving pain and inflammation associated with plantar fasciitis/fasciosis and Achilles tendonitis/tendonosis.

BACKGROUND OF INVENTION

The plantar fascia is a ligament that runs along the bottom of the foot and connects the heel bone (calcaneus) to the base of the toes. It is a thick fibrous band of connective tissue that can stretch slightly. The plantar fascia supports the arch of the foot and facilitates foot movement.

Plantar fasciitis is characterized by pain and inflammation of the plantar fascia associated with microscopic tears at the origin or insertion of the plantar fascia on the heel bone. This microtearing on the cellular level leads to an inflammatory response and concomitant pain usually localized to the plantar medial heel region. Longstanding cases of plantar fasciitis often demonstrate more degenerative changes than inflammatory changes, in which case they are termed plantar fasciosis.

Plantar fasciitis usually affects one foot, although it can occur in both feet simultaneously. Plantar fasciitis pain is often most intense with the first steps of the day. In addition, it can be triggered by long periods of standing or getting up from a seated position. Another symptom associated with plantar fasciitis is decreased dorsiflexion of the ankle. Plantar fasciitis occurs in 2 million Americans a year and in 10% of the U.S. population over a lifetime. Activities such as long-distance running, ballet dancing and dance aerobics place a great deal of stress on the heel and plantar fascia. As a result, participants are more susceptible to plantar fasciitis. Occupations in which workers walk or stand for long periods, especially on hard surfaces, are associated with an increased incidence of plantar fascia injuries. Moreover, obesity is a risk factor.

The Achilles tendon is the large tendon in the back of the ankle that serves to attach the gastrocnemius (calf) and soleus muscles to the heel bone (calcaneus). It is the thickest and strongest tendon in the body. This tendon is approximately 15 cm. (6 in.) long, and runs from the middle of the calf to the heel.

Achilles tendonitis (also Achilles tendinopathy) is characterized by irritation and inflammation of the Achilles tendon. It is a common injury among recreational athletes and tends to be the result of overuse in less than ideal conditions. Achilles tendonosis is associated with chronic Achilles swelling and pain as a result of degenerative, microscopic tears within the tendon. Similar to plantar fasciitis/fasciosis, patients with Achilles tendonitis/tendonosis tend to experience pain after first walking in the morning and when standing after prolonged time in a seated position.

SUMMARY OF THE INVENTION

The present invention is directed to an ankle brace that heals and supports the plantar fascia and Achilles tendon. According to one aspect of the invention, the ankle brace includes a U-shaped pneumatic air bladder which surrounds the plantar fascia. The U-shape design of the air bladder creates a cushion around the plantar fascia, thereby lifting the foot upward without disturbing true walking motion and causing further discomfort of the heel. Furthermore, the cushion serves to lift the heel slightly which offloads the weight on the inflamed region of the plantar fascia insertion at the heel bone and decreases pain. Since pressure is relieved at the insertion point, the injury can heal slowly, and the patient is not required to disturb his daily routine.

According to another aspect of the instant invention, the ankle brace includes a U-shaped pneumatic air bladder wherein both ends of the U-shaped bladder are pneumatically coupled to two air bladders on either side of the Achilles tendon. During the gait cycle, the air is displaced from the plantar foot plate for massaging the insertion of the plantar fascia from distal to proximal. The pressurized air is displaced proximally into dual Achilles bladders maximally inflating these bladders and massaging the Achilles tendon. The motion of the air flow from distal to proximal effectively massages the inflammatory fluid from the underlying soft tissue structures of the plantar fascia and the Achilles tendon. This massaging action thereby aids circulation and decreases inflammatory fluid.

According to another aspect of the present invention, the ankle brace includes an U-shaped air bladder pneumatically coupled to dual air chambers held rigidly against the body part in its correct position. A hook and loop strap secures the brace tightly to the ankle joint providing reduction in ankle motion, sufficient compression of the Achilles air chambers and adjustability of the proximal brace for swelling and comfort. A spandex sleeve surrounding the top of the foot secures the brace to the mid-foot allowing for swelling and keeping the brace in the correct anatomic position. The dual Achilles air chambers include foam and plastic sheets. The foam provides memory to the air chambers to aid in inflation and lifting of the plantar fascia insertion on the foot plate. The plastic sheets provide for semi-rigid support of the ankle structures thus improving the function of the brace. They also provide added compression of the proximal air chamber to increase resistance in the proximal chamber to overinflate the distal chambers at patient discretion. The dynamic nature of the overall brace works to pneumatically massage the desired anatomic structures while giving support to the foot and ankle and thereby reduce pain.

According to another aspect of the invention, there is described a medical device for treating a lower extremity of a user. The medical device includes a foot sleeve having a heel portion and an arch portion, an ankle sleeve coupled to the foot sleeve, and a pneumatic air bladder system. The air bladder system is made up of a substantially U-shaped air chamber positioned in the foot sleeve, the U-shaped air chamber having a first arm extending within a first lateral portion of the arch portion, a second arm extending within a second lateral portion of the arch portion and a third arm coupling a distal end of the first arm to a distal end of the second arm. A pair of bilateral, elongate air chambers are located in the ankle sleeve and fluidly coupled to the U-shaped air chamber. Two tapered communicating channels connect the U-shaped air chamber to the pair of bilateral, elongate air chambers. The ankle sleeve may be constructed substantially of polymethacrylate, and the foot sleeve may be constructed substantially of spandex. A strap is provided for selectively enclosing the ankle sleeve around a user's ankle.

According to yet another aspect of the invention, there is provided a method of treating a lower extremity of a user. The method includes providing a medical device including a foot sleeve, an ankle sleeve coupled to the foot sleeve and a pneumatic air bladder system, the pneumatic air bladder system including a U-shaped air chamber positioned in the foot sleeve and a pair of bilateral, elongate air chambers located in the ankle sleeve and fluidly coupled to the U-shaped air chamber and encircling the user's foot with the foot sleeve and the user's ankle with the ankle sleeve. In so doing, the pair of bilateral, elongate air chambers are arranged to apply pressure to the user's Achilles tendon, while the U-shaped air chamber is arranged to apply pressure bilaterally along the user's heel and arch and medially along a mid-foot portion of the user's foot.

DETAILED DESCRIPTION OF THE DRAWINGS

FIGS. 1 through 7 depict an ankle brace 1 that heals and supports the plantar fascia and the Achilles tendon of a user's foot. The following is a description of a preferred embodiment of the instant invention.

Figure 4:
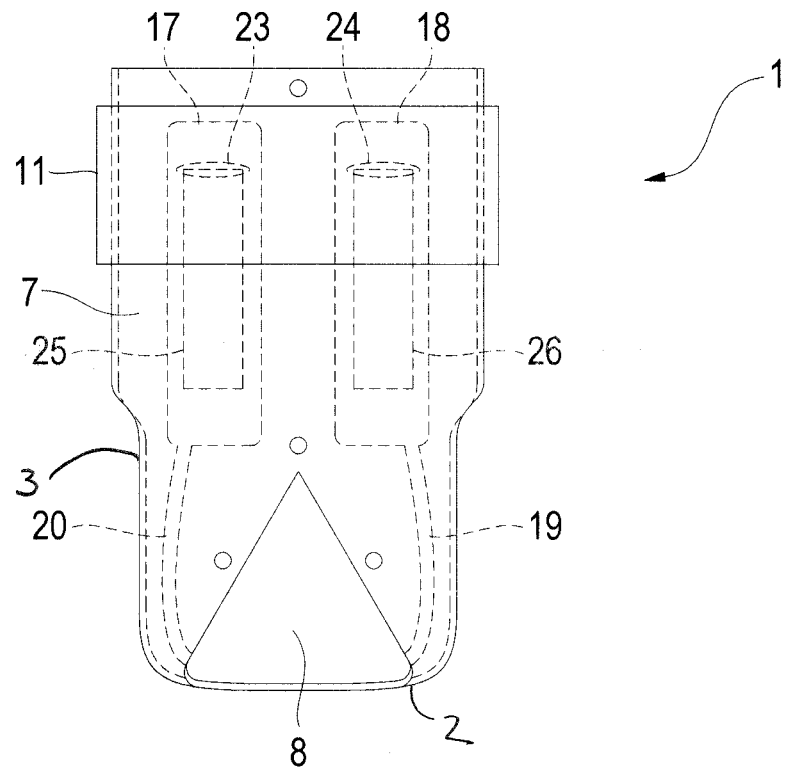
FIG. 4 is an elevational view of a rear of the ankle brace of FIG. 1 with the pneumatic air bladder in phantom.

Ankle brace 1 includes a foot plate portion 2 and an ankle portion 3. In a preferred embodiment, ankle brace 1 is made of polymethacrylate. The foot plate portion 2 of the brace contains a spandex sleeve 4 which surrounds the mid-foot of the user and secures the foot to the brace. The sleeve 4 has a distal opening 5 through which the forefoot extends and a proximal opening 6 through which the heel extends. The ankle portion 3 of the brace includes a rear portion 7 which covers the posterior portion of the ankle. This rear portion 7 is approximately seven inches tall from the foot plate 2 to the uppermost edge of the brace to ensure complete coverage of the ankle and the Achilles tendon. The brace 1 has an opening 8 through which the heel extends. The rear portion 7 has two slits 9 and 10 which accommodate a strap 11 which wraps around the posterior surface of 7 as seen in FIG. 4. In one embodiment of the instant invention, the strap 11 includes a first side and a second side. The first side contains a loop material 13 and the second side contains a strip of fastening hook material 12. Hook and loop material sold under the trademark VELCRO® can be used for this purpose. The strap 11 with the hook and loop closure 12 and 13 secures the ankle portion 3 of the brace to the user's foot.

Figure 1:
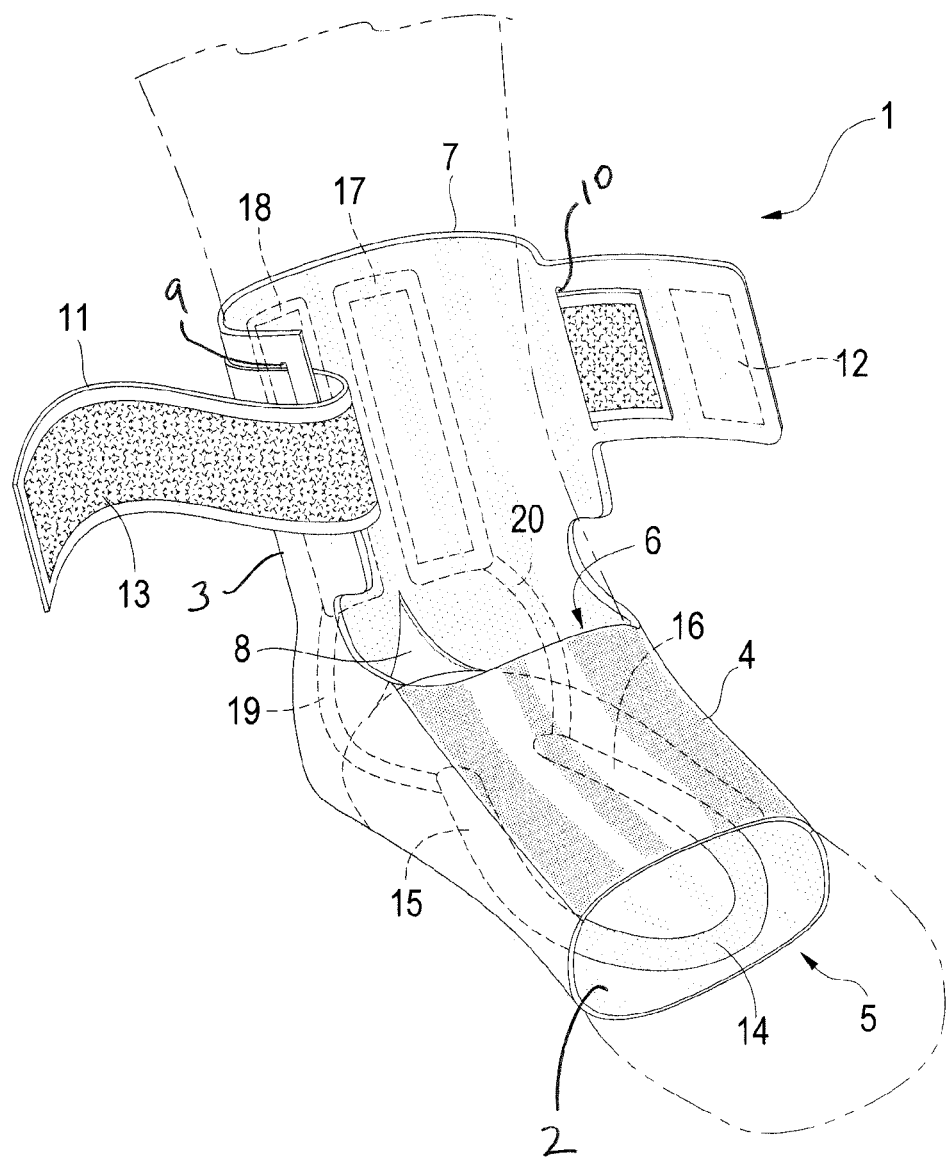
FIG. 1 is a perspective view of an ankle brace in accordance with a preferred embodiment of the present invention with a pneumatic air bladder in phantom.
Figure 2:
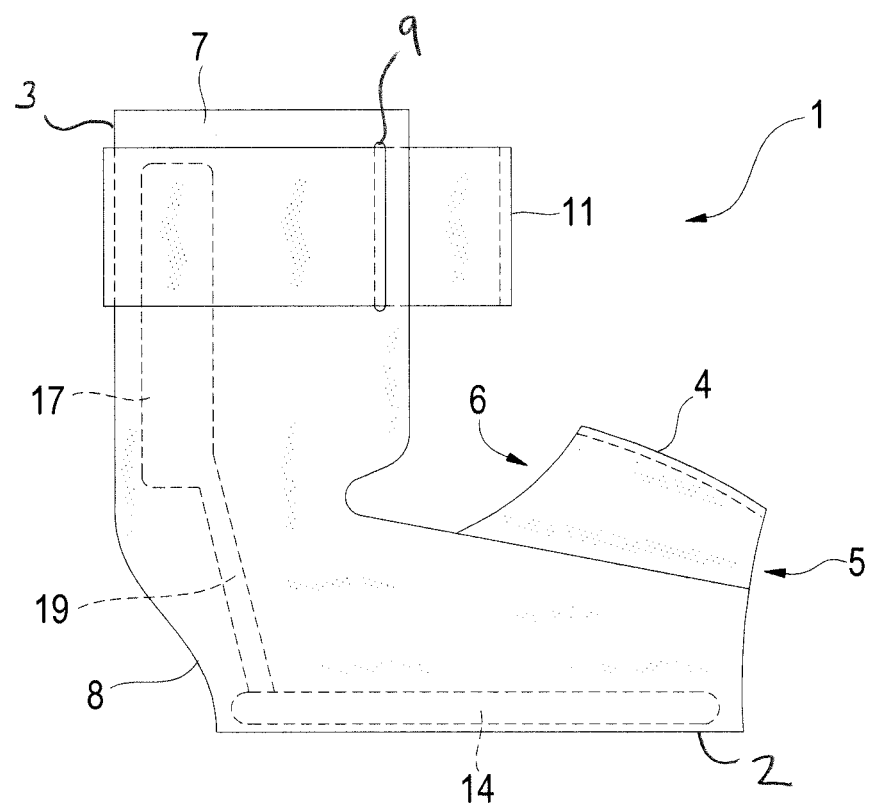
FIG. 2 is an elevational view of a side of the ankle brace of FIG. 1 with the pneumatic air bladder in phantom.
Figure 3:
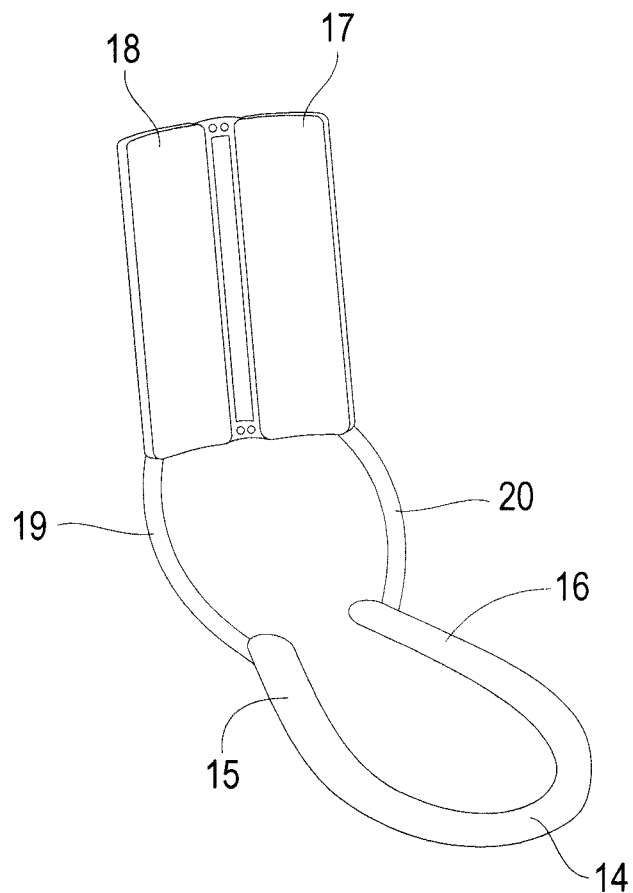
FIG. 3 is a perspective view of the pneumatic air bladder of FIG. 1.
Figure 5:
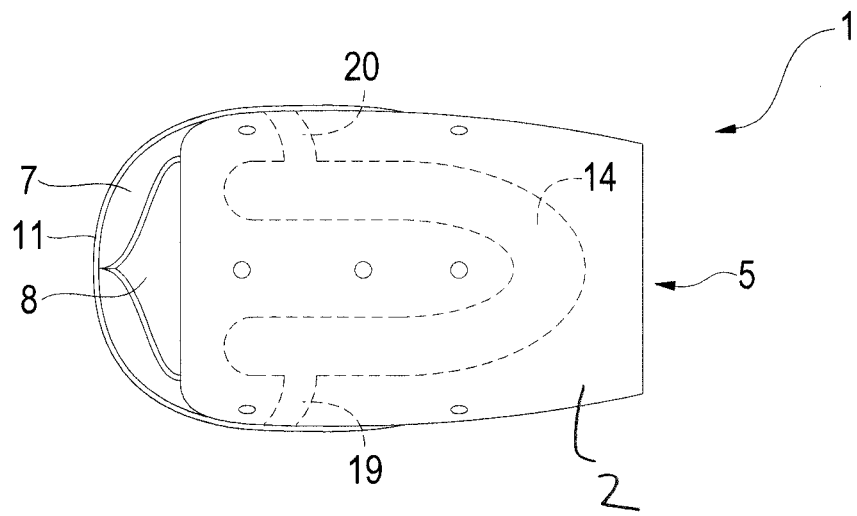
FIG. 5 is a plan view of a bottom of the ankle brace of FIG. 1 with the pneumatic air bladder in phantom.

The ankle brace 1 further includes a single pneumatic air bladder system depicted in FIGS. 3 through 5. This air bladder comprises a U-shaped air cushion 14 which when properly secured to a foot surrounds the plantar fascia and creates a cushion for the plantar fascia origin at the heel bone and lifts the heel upward. Its optimal anatomical design serves to relieve pressure at the plantar fascia insertion point and lessen the pain associated with plantar fasciitis. Furthermore, the U-shaped chamber does not interfere with the user's natural walking gait which could further irritate the medial foot and plantar arch.

Both ends 15 and 16 of the U-shaped air chamber are pneumatically coupled to large air chambers 17 and 18 via tapered communicating channels 19 and 20. In a preferred embodiment, the single air bladder system including the U-shaped portion 14, the dual air chambers 17 and 18, and the communicating channels 19 and 20 is fabricated from polyethylene and assembled via radio frequency plastic welding using methods well known to those skilled in the art.

The ankle brace 1 of the instant invention encompasses the plantar fascia insertion and surrounds the Achilles tendon with a single pneumatic air bladder system. This bladder provides a pulsatile air flow over the plantar fascia insertion and Achilles tendon during the gait cycle. This is accomplished via the unique shape of the bladder and its position on the foot and ankle. The U-shaped chamber 14 surrounds the insertion of the plantar fascia while standing. This chamber, secondary to its inflation, lifts up on the foot at the plantar heel thus offloading the insertion point of the plantar fascia. Upon heel lift, the air from the proximal chambers 17 and 18 begins to maximally inflate the distal chamber 14 secondary to the reduction in resistance in the distal chamber 14. As the foot begins to perform a heel strike, the air begins to compress in the distal chamber 14 and flow to areas of less resistance, the proximal chambers 17 and 18. This flow of air causes the chambers to expand and contract thus massaging the underlying body part. The tapered communicating channels 19 and 20 increase the velocity and compression of the air during motion to and from the distal chamber 14 and the proximal chambers 17 and 18.

According to another aspect of the present invention, the proximal air chambers 17 and 18 contain a durable foam type material seated inside the bladder. The foam material provides memory to the air chambers to aid in inflation and lifting of the plantar fascia. In addition, the proximal bladders 17 and 18 contain openings 23 and 24 under the strap 11 through which polyethylene extruded plastic sheets 25 and 26 provide for semi-rigid support of the ankle structures thus improving the function of the brace. The plastic sheets also provide added compression of the proximal air chambers 17 and 18 to increase resistance in said chambers which serves to further inflate the distal chamber 14.

Figure 6:
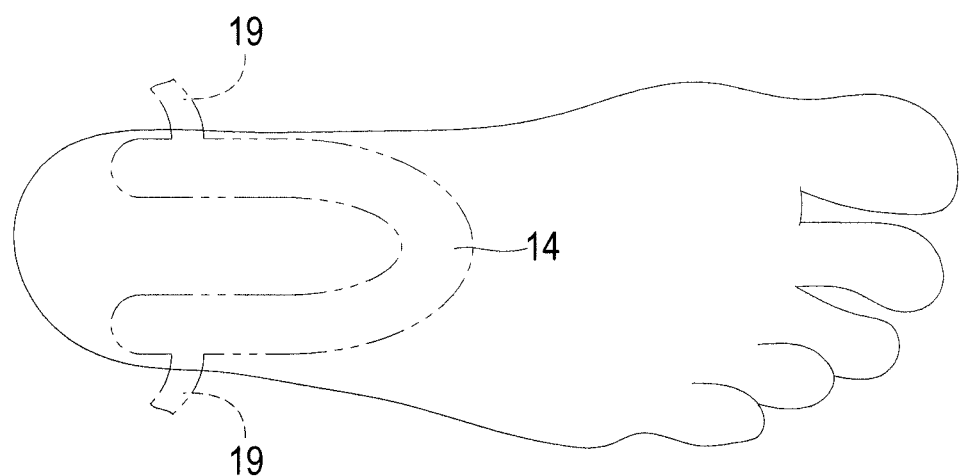
FIG. 6 is a plan view of a bottom of user's foot showing the arrangement of the pneumatic air bladder of FIG. 1 relative to the user's foot.
Figure 7:
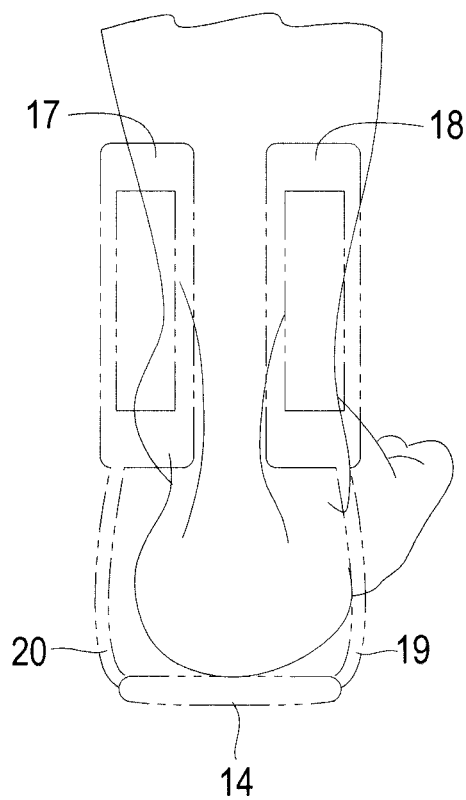
FIG. 7 is an elevational view of a rear of a user's ankle showing the arrangement of the pneumatic air bladder relative to the user's ankle.

According to another aspect of the instant invention, a person suffering from plantar fasciitis and/or Achilles tendonitis would don the foot plate portion 2 of the brace 1 by slipping the spandex sleeve 4 over the mid-foot. Referring to FIGS. 6 and 7, the brace 1 would come to a stop on the mid-foot at the correct position based upon the size of the foot and the size of the brace. The proximal portion 3 of the brace is then secured to the anterior portion of the ankle by the hook and loop strap 11 in a manner which satisfies the user's comfort. The user would wear a shoe over the brace and return to normal daily activities. During the gait cycle, the air is displaced from the plantar foot plate massaging the insertion of the plantar fascia from distal to proximal. The pressurized air is displaced proximally into dual Achilles bladders maximally inflating these bladders and massaging the Achilles tendon. The motion of the air flow from distal to proximal effectively massages the inflammatory fluid from the underlying soft tissue structures of the plantar fascia and the Achilles tendon. This massaging action thereby aids circulation and decreases inflammatory fluid. The dynamic nature of the overall brace works to pneumatically massage the desired anatomic structures while giving support to the foot and ankle.

As will be apparent to one skilled in the art, various modifications can be made within the scope of the aforesaid description. Such modifications being within the ability of one skilled in the art form a part of the present invention and are embraced by the claims below.

The invention claimed is:

1. A medical device for treating a lower extremity of a user comprising:
   a foot sleeve having a length configured for extending along a longitudinal axis of a user's foot, a heel portion and an arch portion,
   an ankle sleeve coupled to the foot sleeve, and
   a pneumatic air bladder system including,
      a substantially U-shaped air chamber positioned in the foot sleeve, the U-shaped air chamber having a first arm extending laterally along the length of the foot sleeve and within a first lateral portion of the arch portion, a second arm extending laterally along the length of the foot sleeve and within a second lateral portion of the arch portion and a third arm coupling a distal end of the first arm to a distal end of the second arm, wherein the entire U-shaped air chamber extends substantially along a plane parallel to the longitudinal axis, and
      a pair of bilateral, elongate air chambers located in the ankle sleeve and fluidly coupled to the U-shaped air chamber.

2. The medical device according to claim 1 wherein the third arm does not extend within the heel portion.

3. The medical device according to claim 1 wherein the third arm extends medially within the arch portion.

4. The medical device according to claim 1 further comprising an elongate space defined and extending between the first arm and the second arm.

5. The medical device according to claim 1 wherein the first arm and the second arm do not extend into a medial portion of the arch portion of the foot sleeve.

6. The medical device according to claim 1 further comprising two tapered communicating air channels fluidly connecting the U-shaped air chamber to the pair of bilateral, elongate air chambers.

7. The medical device according to claim 1 wherein the ankle sleeve is constructed substantially of polymethacrylate.

8. The medical device according to claim 7 wherein the foot sleeve is constructed substantially of spandex.

9. The medical device according to claim 1 wherein the ankle sleeve extends approximately 7 inches from the foot sleeve to an uppermost edge of the brace.

10. The medical device according to claim 1 further comprising a strap configured for selectively enclosing the ankle sleeve around the user's ankle.

11. The medical device according to claim 10 wherein the strap is positioned behind the pair of bilateral, elongate air chambers.

12. The medical device according to claim 1 wherein the pneumatic air bladder system is constructed substantially of polyethylene.

13. The medical device according to claim 1 wherein the pneumatic air bladder system contains a foam material.

14. The medical device according to claim 1 wherein the pneumatic air bladder system includes polyethylene extruded plastic sheets.

15. A method of treating a lower extremity of a user comprising
   providing a medical device including a foot sleeve, an ankle sleeve coupled to the foot sleeve and a pneumatic air bladder system, the pneumatic air bladder system including a U-shaped air chamber positioned in the foot sleeve and a pair of bilateral, elongate air chambers located in the ankle sleeve and fluidly coupled to the U-shaped air chamber,
   encircling the user's foot with the foot sleeve and the user's ankle with the ankle sleeve,
   arranging the pair of bilateral, elongate air chambers to apply pressure to the user's Achilles tendon, and
   arranging opposing arms of the U-shaped air chamber to extend alongside a longitudinal axis of the user's foot thereby applying pressure bilaterally along a bottom surface of the user's heel, bilaterally along the user's arch and medially along a mid-foot portion of the user's foot, wherein the entire U-shaped air chamber extends substantially along a plane parallel to the longitudinal axis.

16. The method according to claim 15 wherein the U-shaped air chamber does not apply pressure to a medial portion of the user's heel.

17. The method according to claim 15 wherein the mid-foot portion includes the arch of the user's foot.

18. The method according to claim 15 further comprising transferring a fluid between the U-shaped air chamber and the pair of bilateral, elongate air chambers.

19. The method according to claim 15 further comprising arranging the U-shaped air chamber to extend laterally adjacent to but not medially across an insertion of the plantar fascia of the user.

20. A method of treating a lower extremity of a user comprising,
   providing a medical device including a foot sleeve, an ankle sleeve coupled to the foot sleeve and a pneumatic air bladder system, the pneumatic air bladder system including a U-shaped air chamber positioned in the foot sleeve and a pair of bilateral, elongate air chambers located in the ankle sleeve and fluidly coupled to the U-shaped air chamber,
   encircling the user's foot with the foot sleeve and the user's ankle with the ankle sleeve,
   arranging the pair of bilateral, elongate air chambers to apply pressure bilaterally to the user's Achilles tendon,
   arranging opposing arms of the U-shaped chamber to extend alongside a longitudinal axis of the user's foot thereby applying pressure bilaterally along a bottom surface of the user's heel, bilaterally along the user's arch and medially along an arch of the user's foot,
   transferring a fluid between the U-shaped air chamber and the pair of bilateral, elongate air chambers,
   wherein the U-shaped chamber does not apply pressure to a medial portion of the user's heel, and wherein the entire U-shaped air chamber extends substantially along a plane parallel to the longitudinal axis.

* * * * *